United States Patent [19]
Bove et al.

[11] Patent Number: 5,447,496
[45] Date of Patent: Sep. 5, 1995

[54] METHOD FOR INPLANTING A SELECTED LIQUID INTO THE COLON

[76] Inventors: Rick L. Bove; Lynne Moretti-Bove, both of 4647 Alta Rica Dr., La Mesa, Calif. 91941

[21] Appl. No.: 228,859

[22] Filed: Apr. 18, 1994

[51] Int. Cl.$^6$ .................................... A61H 31/00
[52] U.S. Cl. ........................... 604/54; 604/49; 604/246
[58] Field of Search ................ 604/19, 27, 28, 30, 604/33, 36, 38, 48, 49, 54, 73, 93, 181, 186, 187, 246, 249, 257, 275, 279

[56] References Cited

U.S. PATENT DOCUMENTS

| | | | |
|---|---|---|---|
| 2,832,341 | 4/1958 | Stack | 604/28 |
| 3,823,714 | 7/1974 | Waysilk et al. | 604/28 |
| 4,036,232 | 7/1977 | Genese | 128/278 |
| 4,447,235 | 5/1984 | Clarke | 604/169 |
| 4,560,378 | 12/1985 | Weiland | 604/83 |
| 4,704,102 | 11/1987 | Guthery | 604/28 |
| 4,874,365 | 10/1989 | Frederick et al. | 604/54 |
| 5,002,528 | 3/1991 | Palestrant | 604/28 |
| 5,049,137 | 9/1991 | Thompson | 604/240 |
| 5,074,842 | 12/1991 | Clayton | 604/54 |

*Primary Examiner*—Corrine Maglione
*Attorney, Agent, or Firm*—John R. Duncan; Frank D. Gilliam

[57] ABSTRACT

A method for accurately and conveniently implanting a selected quantity of a liquid into the colon. The apparatus comprises a positive displacement, plunger type, syringe for holding and dispensing a selected quantity of liquid, a tubular connecter at the outlet end of the syringe, a valve connected to the bore of the connector for selectively connecting the bore to the atmosphere and a tube attached to the tubular connector. A nozzle may be used to attach the tubular connector to a plastic tube which is in turn attached to a rectal catheter. In use, a selected quantity of liquid is drawn into the syringe, the tube is connected thereto, the catheter is inserted well into the colon and the syringe plunger is pressed to dispense the liquid into the tube. Since the tube is then still filled with liquid, the valve is opened and the atmosphere is connected to the tube. In some cases the remaining liquid will drain into the colon by gravity. In most cases, it is preferred to draw air back into the syringe with the valve open, close the valve and press the syringe plunger to drive the remaining liquid into the colon under the force of air expelled by the syringe.

3 Claims, 1 Drawing Sheet

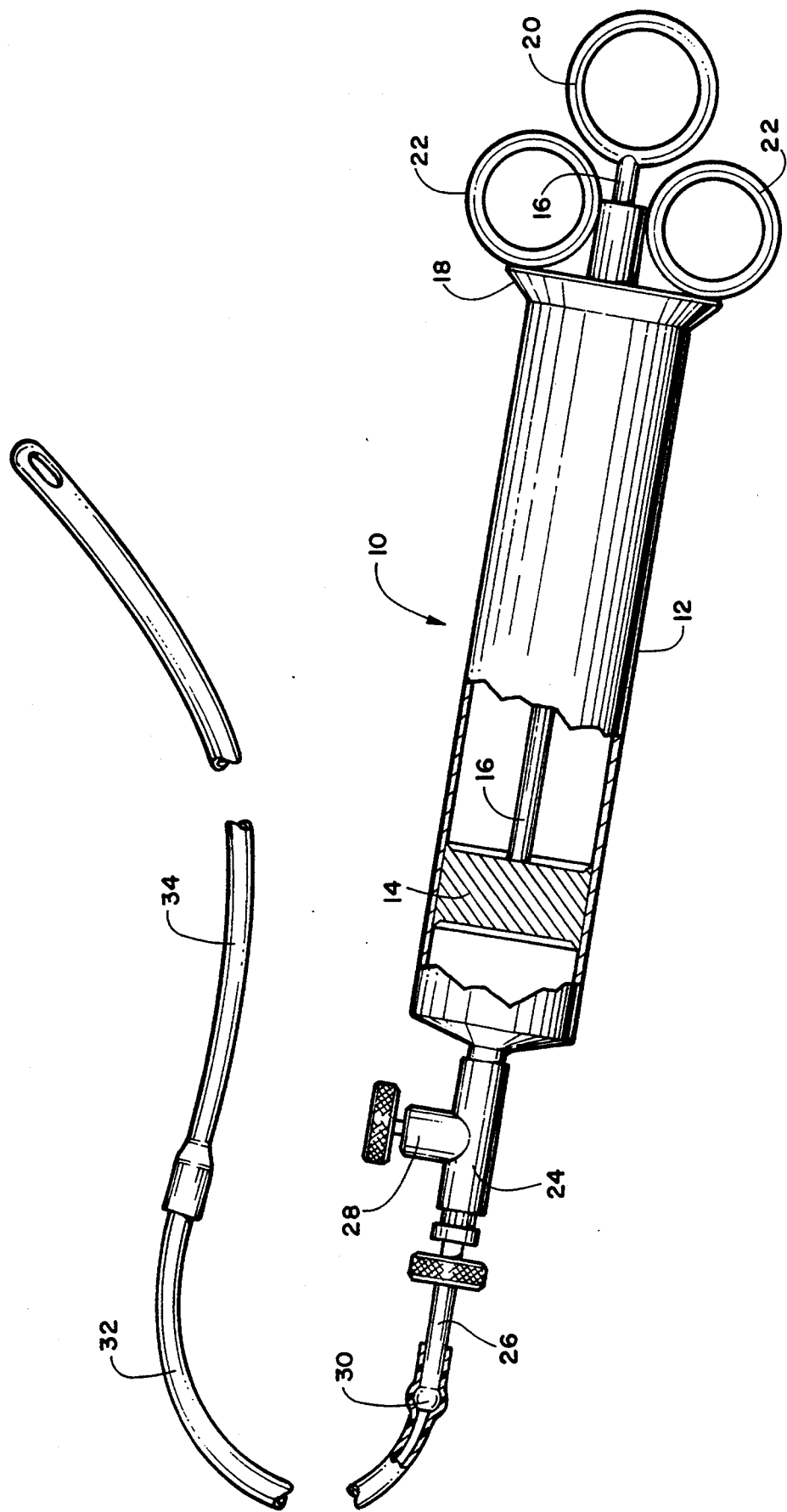

METHOD FOR INPLANTING A SELECTED LIQUID INTO THE COLON

BACKGROUND OF THE INVENTION

This invention relates in general to methods and apparatus for delivering a liquid into the colon and, more specifically to a method and apparatus for fully delivering a selected quantity of a liquid well into the colon.

Conventionally, when it is desired to implant a selected liquid, solution or mixtures of particulate materials in a liquid carrier, well up into the colon, a plastic tube is connected between a rectal catheter and a bucket-like liquid container, the catheter is inserted as far as necessary into the colon and the bucket is elevated to allow the liquid to flow into the colon using the force of gravity.

This arrangement, while in general use, has a number of problems. The equipment is cumbersome and spillage or inadvertent release of liquid often occurs. A clip on the plastic tube serves as a valve so that liquid flow begins only when the clip is released, after the other components are ready. The clip may leak and is often difficult to manipulate.

With small amounts of liquid, there may not be sufficient hydrostatic head to force all of the liquid through the catheter, especially when the liquid is relatively thick or is a mixture of particles in the liquid. Also, bubbles in the tube will often prevent flow of the liquid. In order to eliminate bubbles, the catheter end must be raised above the liquid level in the container, the clip released, the catheter lowered until a free flow of liquid from the catheter begins, then the clip replaced. Where a reasonably precise amount of liquid is to be administered, the loss of varying amounts of liquid during bubble elimination will make administration of precise amounts very difficult. Furthermore, bubbles may later enter through the catheter tip if the catheter tube is inadvertently squeezed and released while beginning insertion into the colon.

Kinks in the catheter tube will also prevent flow of the liquid by gravity and are often difficult to prevent or eliminate. Often, the catheter must be removed resulting in considerable spillage of the liquid being implanted, with the implantation then repeated. The spillage is both messy and expensive where a costly material is being implanted.

Attempts have been made to use a rubber bulb type syringe connected to the catheter to reduce some of these problems. However, it is not possible to entirely empty the syringe and liquid is likely to remain in the syringe, tube and catheter, resulting in incomplete implantation, an inaccurate and indefinite quantity implanted, and a waste of material not implanted.

Thus, there is a continuing need for improved devices for implanting various liquids in the colon that can implant a precise desired amount of liquid, that use all of the liquid to be implanted without waste, that can perform complete implants despite bubbles or kinks in the tube or catheter and that can successfully implant small, precise quantities of liquids by positive pressure rather than gravitational forces.

SUMMARY OF THE INVENTION

The above-noted problems, and others, are overcome in accordance with this invention by an apparatus for implanting liquids well into the colon which comprises a positive displacement, plunger-type, syringe, a nozzle on the syringe outlet for expelling the contents of the syringe, a catheter connected to the nozzle to form a continuous fluid-flow path from the syringe to the outlet end of the catheter, and a valve in the fluid-flow path for selectively opening and closing a connection between the atmosphere and said path.

For optimum performance, the valve is connected between the nozzle and the syringe. The valve is preferably biased, such as by a spring, to a closed position which prevents atmospheric air from entering the fluid-flow path. When the valve is moved to the open position, such as by pressing a button against said biasing force, outside air can enter the fluid flow path.

In use, typically, the syringe is filled with the desired quantity of the liquid to be implanted, the catheter is connected to the nozzle (typically with a tube of convenient length between nozzle and catheter) and the plunger is pressed to expel liquid into the tube and out the catheter outlet. When the plunger is fully pressed to fully empty the syringe, liquid remains in the catheter and any intervening tube. The valve is then opened, allowing air to enter the system. In some cases, gravity will be sufficient to allow remaining liquid in the catheter and tube to pass out of the catheter.

In most cases, positive pressure to assure complete emptying of the catheter and tube will be preferred. In that circumstance, with the valve open, the syringe plunger will be retracted to draw air into the syringe through the valve. The valve is closed and the syringe plunger is pressed to push air into the tube and catheter behind any remaining liquid. Generally, when the catheter is emptied, the person pressing the plunger will immediately feel the decrease in back pressure. In any event, the introduction of a small amount of air into the colon will not have adverse affects, since a normal colon often contains gas bubbles.

Any suitable liquid may be used with this system. The liquid may carry a medicine or other beneficial liquid or particulate material. Applicants make no claims or assertion that this system will cure any disease or condition. Rather, applicants have provided a convenient, accurate and practical apparatus for delivering any suitable liquid well into the colon.

Among the liquids that may be delivered using the method and apparatus of this invention are the wheat-grass juice implants described in detail by Richard Walters, in the book "Options: The Alternative Cancer Therapy Book", Paragon Press, Honesdale, Pa., 1993. Problems with prior implant techniques are apparent from the discussion on pages 12 and 13 of the Workbook and Study Guide", Mark Solomon, from The Optimum Health Institute of San Diego. Others have used rectal implants of very finely divided shark cartilage as rectal implants (also commonly referred to as "retention enemas") to increase the absorption of the cartilage protein, as described by Dr. I. William Lane and Linda Comac their book "Sharks Don't Get Cancer, pp. 94–95, 1992.

BRIEF DESCRIPTION OF THE DRAWING

Details of the invention, and of preferred embodiments thereof, will be further understood upon reference to the drawing which shows the assembly of positive displacement syringe, air valve, tube and catheter according to this invention.

DETAILED DESCRIPTION OF PREFERRED EMBODIMENTS

As seen in the Figure, syringe 10 is a conventional plunger type, positive-displacement syringe having a generally cylindrical housing 12 containing a plunger 14 which is a tight friction fit within housing 12 and may have a sealing agent, such as a water insoluble grease, between the plunger and the interior wall of housing 12. Plunger 14 is moved lengthwise of housing 12 by a rod 16 which passes through first end 18 of syringe 10 and is secured to a ring 20. Two other rings 22 are secured to housing end 18 so that a user can withdraw the plunger by pulling on ring 20, then insert two fingers in rings 22 and one in ring 20 and easily dispense the contents of syringe 10 by pushing plunger 14 inwardly.

A connector 24 is secured at one end to the outlet of syringe 10 and at the opposite end to a nozzle 26. Preferably connector 24 has male threads at one end and female threads at the other conforming to the conventional threads on nozzle 26 and syringe 10 that would ordinarily be used to thread the nozzle directly into the syringe. A conventional push-button, pressure relief or vacuum relief type valve 28 is connected to the bore through connector 24. Valve 28 is biased, such as by a compression spring (not shown) toward a closed position. Pressing the valve button connects the connector bore to the outside atmosphere.

Nozzle 26 is of conventional design and preferably has a bulbous end 30 to assure a tight, non-slip, connection to a tube 32, typically a conventional vinyl tube.

Tube 32 has a diameter which permits it to be pressed into the slightly narrower inlet end of catheter 34 to assure a non-slip connection. Any suitable catheter may be used. Typically rectal catheters have diameters of about ¼ inch and lengths of about 12 to 24 inches, although any suitable dimensions may be used. Catheter 34 typically has an axial opening at the outlet end and/or a side opening near the outlet end.

In use, nozzle 26, connector 24 and syringe 10 are assembled as shown. Nozzle 26 is dipped into a quantity of liquid to be implanted in the colon and plunger 20 is withdrawn to pull the desired quantity of liquid into the syringe. Nozzle 26 is inserted into tube 32. Preferably, ring 20 is pressed to move plunger 14 inwardly sufficiently to fill tube 32 and catheter 34 with liquid, as evidenced by the appearance of liquid at the catheter outlet. Catheter 34 is then inserted into the rectum the desired distance, typically about 2 to 24 inches.

Plunger 14 is moved inwardly to dispense the desired quantity of liquid, at which point tube 32 and catheter 34 are still filled with liquid. Valve 28 is then opened, allowing outside air to enter the bore in connector 24 thereby releasing any vacuum pressure that prevents the tube 32 and catheter 34 from draining. In some cases, gravity may be sufficient to completely drain tube 32 and catheter 34 into the colon. However, to assure complete emptying, it is preferred that plunger 14 be retracted with valve 28 open, at least partially filling the syringe with air. The plunger is then pressed inwardly, causing the air within the syringe to force any remaining liquid in tube 32 and catheter 34 into the colon. Back pressure will drop significantly when all of the liquid has been expelled from the catheter, so the user will know when to stop pressing plunger 14 inwardly. There is no problem if a small quantity of air is expelled into the colon.

Any air bubbles in tube 32 and catheter 34 will not hinder the implantation, since the positive pressure will drive them along with the liquid. Similar, most kinks that might occur in catheter 34, which is generally very flexible, will be straightened out by the pressure of the liquid as driven by the syringe plunger. Since all liquid will be implanted, very precise control of the quantity of liquid is possible, which can be quite important where the liquid contains a medical ingredient.

While certain preferred materials, dimensions and arrangements have been detailed in conjunction with the above description of preferred embodiments, those can be varied, where suitable, with similar results. For example, if desired tube 32 could be eliminated where a longer catheter 34 is used. Other applications, variations and ramifications of this invention will occur to those skilled in the art upon reading this disclosure. Those are intended to be included within the scope of this invention as defined in the appended claims.

We claim:

1. The method of implanting a selected liquid into the colon which comprises:
   connecting a first end of an elongated tubular means to an outlet end of a positive displacement, plunger type, syringe filled with a selected quantity of a liquid;
   providing a valve means selectively communicating between the atmosphere and a fluid flow path through said tubular means;
   inserting a second end of said tubular means into the colon at least about 2 inches;
   pressing the syringe plunger to expel liquid into said tubular means;
   opening said valve and withdrawing said plunger to draw air from the atmosphere into said syringe;
   pressing said plunger to force air into said tubular means to expel substantially all of the liquid into the colon.

2. The method according to claim 1 further including assembling said tubular means by:
   providing a connector tube carrying said valve and having a first end connected to said syringe outlet end and a second end;
   connecting a first end of a plastic tube having first and second ends to said second end of said connector tube; and
   connecting a first end of a rectal catheter to said second end of said plastic tube.

3. A method of assembling a device for implanting a selected liquid into the colon which comprises:
   providing a positive displacement, plunger, type syringe having an outlet end;
   providing a tubular connector having first and second ends and a valve means on said connector communicating between the interior of said tubular connector and the atmosphere, spring loaded to close said communication and manually operable to establish said communication;
   securing said first end of said tubular connector to said syringe outlet end;
   connecting a first end of a plastic tube having first and second ends to said second end of said tubular connector; and
   connecting a first end of a rectal catheter having first and second ends to said second end of said plastic tube;
   whereby the resulting assembly is capable of dispensing liquid from said syringe into said tubular connector, plastic tube and rectal catheter and said tubular connector, plastic tube and rectal catheter can be drained by elevating said syringe and opening said valve.

* * * * *